(12) United States Patent
Sundaram

(10) Patent No.: US 11,225,609 B2
(45) Date of Patent: Jan. 18, 2022

(54) CO-PROCESSING OF WASTE PLASTIC WITH BIOMASS

(71) Applicant: ExxonMobil Research and Engineering Company, Annandale, NJ (US)

(72) Inventor: Narasimhan Sundaram, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 5 days.

(21) Appl. No.: 17/019,803

(22) Filed: Sep. 14, 2020

(65) Prior Publication Data

US 2021/0130698 A1 May 6, 2021

Related U.S. Application Data

(60) Provisional application No. 62/929,364, filed on Nov. 1, 2019.

(51) Int. Cl.
| | | |
|---|---|---|
| *C10B 53/02* | (2006.01) | |
| *C10B 53/07* | (2006.01) | |
| *B01D 53/02* | (2006.01) | |
| *C07C 29/151* | (2006.01) | |

(52) U.S. Cl.
CPC .............. *C10B 53/02* (2013.01); *B01D 53/02* (2013.01); *C07C 29/1518* (2013.01); *C10B 53/07* (2013.01); *B01D 2253/1124* (2013.01); *B01D 2256/16* (2013.01); *B01D 2257/502* (2013.01); *B01D 2257/504* (2013.01); *B01D 2259/40086* (2013.01)

(58) Field of Classification Search
CPC ... C01B 53/02; C01B 53/07; C01B 2203/043; C01B 2203/0475; B01D 2253/1124; B01D 2256/16; B01D 2257/502; B01D 2257/504; B01D 2259/40086; C07C 29/1518
See application file for complete search history.

(56) References Cited

U.S. PATENT DOCUMENTS

| | | | |
|---|---|---|---|
| 7,976,797 | B2 | 7/2011 | Chun et al. |
| 2018/0036674 | A1 | 2/2018 | Sundaram |
| 2018/0237322 | A1 | 8/2018 | Lewis |
| 2019/0153331 | A1 | 5/2019 | Barrai et al. |

FOREIGN PATENT DOCUMENTS

| | | |
|---|---|---|
| WO | 2015106790 A1 | 7/2015 |
| WO | 2018069794 A1 | 4/2018 |
| WO | 2018107204 A1 | 6/2018 |

*Primary Examiner* — Jafar F Parsa
(74) *Attorney, Agent, or Firm* — Kristina Okafor

(57) ABSTRACT

Systems and methods are provided for co-processing of plastic waste with biomass to generate gas phase product streams with improved properties. The systems and methods can include having a high temperature swing adsorption process integrated with a pyrolysis process, gasification process, or other thermal conversion process, so that $CO_2$ can be removed from at least a portion of the effluent. This can facilitate capture of $CO_2$ when using pyrolysis, gasification, or other thermal conversion to generate a hydrogen-containing stream. Additionally, the integrated system and/or method can allow for production of multiple product streams having desirable ratios of hydrogen to carbon oxides.

20 Claims, 1 Drawing Sheet

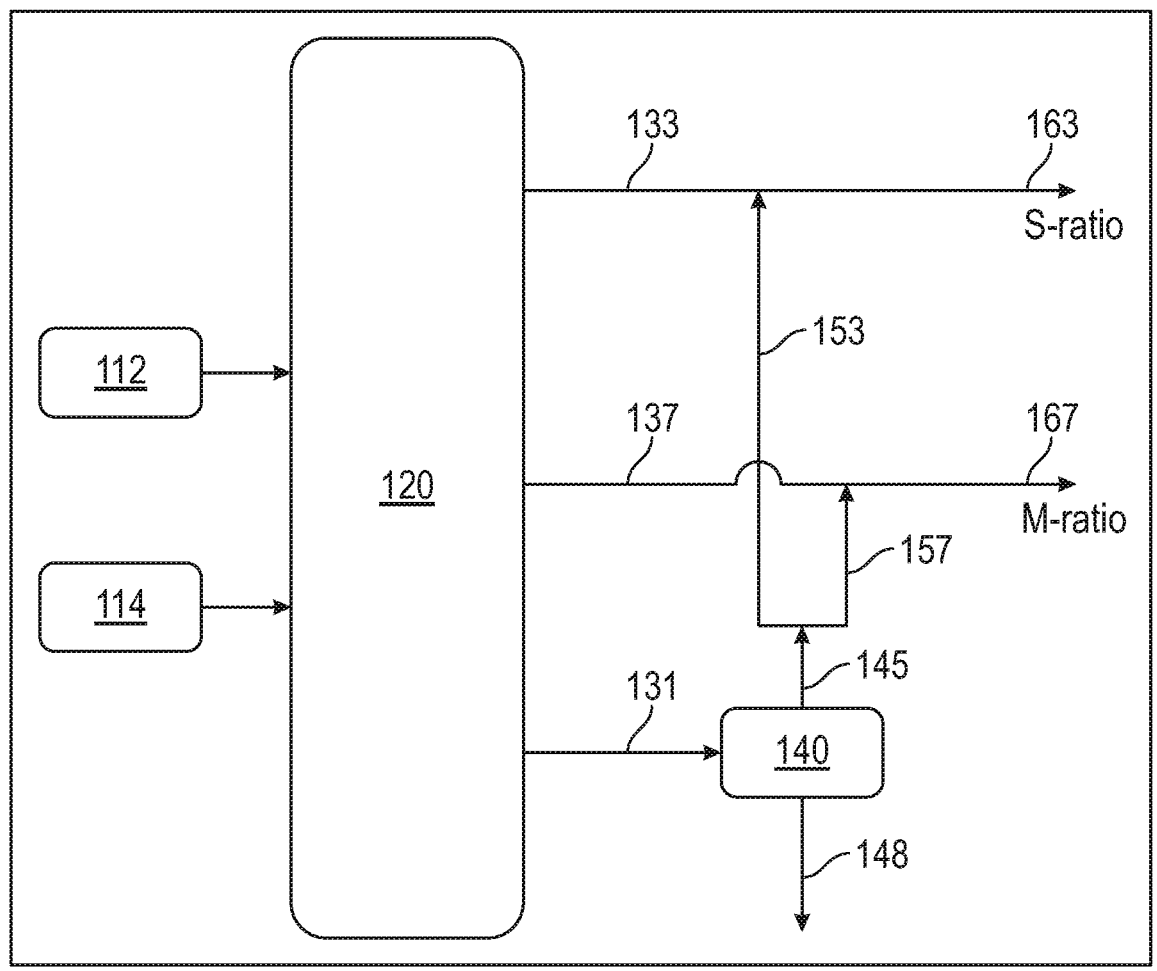

CO-PROCESSING OF WASTE PLASTIC WITH BIOMASS

CROSS-REFERENCE TO RELATED APPLICATIONS

This application claims the benefit of priority from U.S. Provisional Application No. 62/929,364 filed Nov. 1, 2019, which is incorporated herein by reference in its entirety.

FIELD OF THE INVENTION

Systems and methods are provided for co-processing of waste plastic with biomass

BACKGROUND OF THE INVENTION

Recycling of plastic waste is a subject of increasing importance. Conventionally, polyolefins in plastic waste are converted by various methods, such as pyrolysis or gasification. While this provides a pathway for using waste plastic, the resulting products from the conversion can vary widely. This is due in part to variations in the nature of available plastic waste. Additionally, providing dedicated equipment for processing of plastic waste can involve substantial additional cost.

One alternative can be to co-process plastic waste with another feedstock. One type of beneficial feedstock for co-processing of plastic waste is a biomass feedstock. Biomass feedstocks can tend to be oxygen rich, while waste plastics have a relatively higher hydrogen content. Co-pyrolysis of a mixed feed of biomass and plastic waste can therefore allow for production of higher quality liquid products. However, such co-pyrolysis can also result in a higher content of CO and/or $CO_2$ in the pyrolysis gas phase products. As a result, the gas phase pyrolysis effluent from conventional co-processing has a ratio of $H_2$ to carbon oxides that is lower than desirable for most types of follow on processes. Conventionally, converting and/or separating the gas phase pyrolysis effluent requires multiple stages, including stages for cooling the effluent to a suitable temperature for separating $CO_2$ from synthesis gas.

What is needed is a flexible separations platform (and methods of using such a separations platform) that can allow for increased uniformity and/or quality in gas phase products from co-processing biomass with waste plastics.

International Publication WO/2015/106790 describes methods for co-pyrolysis of biomass and plastic waste. Due to the low boiling point of plastic waste, portions of melted plastic waste can evaporate and/or become entrained in the gas phase pyrolysis effluent without being pyrolyzed. In order to avoid this a method is proposed for introducing the plastic waste in a counter-current manner, so that plastic waste entrained in the gas phase pyrolysis effluent is reduced or minimized.

U.S. Patent Application Publication 2018/0036674 describes systems and methods for separating $CO_2$ from synthesis gas using pressure swing adsorption at elevated temperature. The separation can be performed at elevated temperature based on use of a mixed metal oxide adsorbent that can selectively adsorb $CO_2$ at temperatures of 300° C. to 600° C.

U.S. Pat. No. 7,976,797 and U.S. Patent Application Publication 2019/0153331 describe examples of reverse flow regenerative reactors.

SUMMARY

In various aspects, a method for forming a plurality of synthesis gas compositions is provided. The method includes exposing a feedstock comprising a mixture of biomass and plastic waste to pyrolysis conditions at a temperature of 500° C. to 1200° C. to form at least a low-hydrogen-content synthesis gas stream. The low-hydrogen-content synthesis gas stream can contain at least $H_2$, CO, and $CO_2$ and/or the low-hydrogen-content synthesis stream can have a molar ratio of $H_2$ to CO of 0.5 to 1.7. At least a portion of the low-hydrogen-content synthesis gas stream can be exposed to an adsorbent at a first adsorbing temperature of 300° C. to 600° C. and a first adsorbing pressure of 1.0 MPa-g or more to form an $H_2$-enriched stream comprising an $H_2$ to CO ratio of 10 or more. A first portion of the $H_2$-enriched stream can be combined with a first bypass portion of the low-hydrogen-content synthesis gas stream to form a first product synthesis gas stream comprising a first $H_2$ to CO ratio of 1.8 or more. Additionally, a second portion of the $H_2$-enriched stream can be combined with a second bypass portion of the low-hydrogen-content synthesis gas stream to form a second product synthesis gas stream comprising a second $H_2$ to CO ratio of 1.8 or more. For example, a first product synthesis gas stream can be formed with an S-ratio suitable for Fischer-Tropsch synthesis and a second product synthesis gas stream can be formed with an M-ratio suitable for methanol synthesis.

BRIEF DESCRIPTION OF THE DRAWINGS

The FIGURE shows a process flow for performing high temperature pressure swing adsorption on the synthesis gas portion of the gas phase effluent from a gasification process.

DETAILED DESCRIPTION

All numerical values within the detailed description and the claims herein are modified by "about" or "approximately" the indicated value, and take into account experimental error and variations that would be expected by a person having ordinary skill in the art.

In various aspects, systems and methods are provided for co-processing of plastic waste with biomass to generate gas phase product streams with improved properties. The systems and methods can include having a high temperature swing adsorption process integrated with a pyrolysis process, gasification process, or other thermal conversion process, so that $CO_2$ can be removed from at least a portion of the effluent without requiring cooling of the effluent to a temperature of 100° C. or less. This can facilitate capture of $CO_2$ when using pyrolysis, gasification, or other thermal conversion to generate a hydrogen-containing stream. Additionally, the integrated system and/or method can allow for production of multiple product streams having desirable ratios of hydrogen to carbon oxides.

In this discussion, pyrolysis generally refers to a process for thermal conversion of a feed to lower boiling products. A pyrolysis effluent (or other thermal conversion effluent) can potentially contain both the components of synthesis gas and hydrocarbons. The hydrocarbons in a pyrolysis effluent can include $C_{4-}$ compounds (light ends), naphtha boiling range compounds, and distillate boiling range compounds. If sufficient oxygen is present in the pyrolysis environment, and if the conditions are sufficiently severe, the process can be referred to as gasification. In a gasification process, the primary products from the process are solid char and synthesis gas components ($H_2$, $H_2O$, CO, and $CO_2$), with less than 5.0 wt % of the pyrolysis product corresponding to hydrocarbons, or less than 1.0 wt %. It is noted that oxygen present within a biomass or plastic waste feed can contribute to the amount of oxygen present in the pyrolysis environment. To the degree atoms other than hydrogen, carbon, and oxygen are present in the pyrolysis environment, other compounds can also be formed, such as sulfur-containing compounds or nitrogen-containing compounds. In this discussion, processing of a mixed feed of biomass and plastic waste will be described based on gasification of the feed. This simplifies the processing of the feed, as a separation is not needed and/or only minimal separation is needed to separate synthesis gas from the hydrocarbon portions of the pyrolysis effluent. However, it is understood that other types of thermal conversion/pyrolysis can be used to generate synthesis gas as the input flow to the high temperature pressure swing adsorption process described herein. In such aspects involving other types of pyrolysis, a separation can be performed on the pyrolysis effluent to separate a fraction containing synthesis gas components from one or more other fluid phase fractions of the pyrolysis effluent. While this may require some cooling and re-heating of the pyrolysis effluent, the additional cooling and re-compression steps required for conventional $CO_2$ separation from synthesis gas can still be avoided. In such aspects, an optional additional separation may be performed on the synthesis gas to remove water from the synthesis gas, such as a separation to reduce the water content of the synthesis gas to 10 vol % or less, or 5.0 vol % or less, or 1.0 vol % or less, such as down to having substantially no water in the synthesis gas after separation and prior to exposure to the high temperature adsorbent.

Pyrolysis (such as gasification) is generally known for co-processing of plastic waste with biomass. However, conventional pyrolysis/gasification methods have suffered from several limitations. Some of the limitations are related to producing high quality synthesis gas streams from the gas phase portion of the pyrolysis or gasification effluent. In particular, the ratio of $H_2$ to CO in a conventional pyrolysis/gasification effluent can tend to be lower than desired. One conventional option for increasing the $H_2$ to CO ratio would be to remove $CO_2$ from the gas phase portion of the effluent, and then use a water gas shift reaction to generate more $H_2$. However conventional methods of removing $CO_2$ typically involve cooling the gas phase effluent to a temperature below 100° C., such as to 30° C. or less. Thus, in order to remove $CO_2$ and then perform water gas shift, the temperature of the gas phase effluent portion would need to be dropped close to ambient temperature, and then re-heated to a temperature of 150° C. or more to perform the water gas shift reaction. This type of temperature cycling requires substantial energy input. Additionally, substantial equipment footprint is required to accomplish the distinct cooling, separation, re-heating, and water gas shift functions.

Another difficulty with pyrolysis (such as gasification) of combinations of biomass with plastic waste is the widely varying content of the resulting synthesis gas. Due to variations in the types of biomass and plastic waste that may be available, the molar ratio of $H_2$ to CO in the gas phase effluent can range from less than 1.0 to up to 1.7. Using a conventional processing train of low temperature $CO_2$ separation and subsequent water gas shift, it is difficult to control the process train to produce a single effluent with a desired synthesis gas ratio. In particular, the severity of at least one of (and possibly both of) the $CO_2$ separation and the water gas shift reaction would need to be modified in order to produce a synthesis gas output with a desired ratio of $H_2$ to CO.

In contrast to conventional methods, in various aspects, the multiple conventional processing stages for removal of $CO_2$ and performing the water gas shift reaction can be replaced by a high temperature pressure swing adsorption (PSA) separation for removal of $CO_2$. In such aspects, the adsorbent used in the pressure swing adsorption process is suitable for $CO_2$ adsorption at temperatures of 350° C. to 500° C., so that any cooling of the gas phase portion of the gasification effluent can be reduced or minimized Additionally, the adsorbent can also provide water gas shift functionality, so that the water gas shift reaction occurs as $CO_2$ is removed from the gas phase effluent. In some aspects, water is not separated from the gas phase pyrolysis effluent prior to exposing the gas phase pyrolysis effluent to the high-temperature pressure swing adsorption process. In other alternative aspects, at least a portion of the water in the gas phase pyrolysis effluent can be separated out prior to the high-temperature pressure swing adsorption process. In such aspects, water desorbed from the adsorbent in the swing adsorber reactor can provide at least a portion of the water that is required for performing the water gas shift reaction.

The ability to perform high temperature $CO_2$ adsorption while simultaneously facilitating the water gas shift reaction can provide a variety of unexpected advantages. In particular, due to the ability to remove $CO_2$ while performing the water gas shift reaction, sufficient $CO_2$ can be removed from the gas phase effluent to form an enriched $H_2$ product. The enriched $H_2$-containing product can have a sufficiently high ratio of $H_2$ to CO that it can be blended with an untreated portion of the gas phase effluent to form a product with desirable or target ratio of $H_2$ to CO.

In some aspects, an additional advantage of the systems and methods described herein is that control of the process for forming the synthesis gas streams can be simplified. Instead of having to modify processing conditions to match variability in the feed, the process can be controlled by controlling the amount of gas phase pyrolysis effluent that is exposed to the high temperature pressure swing adsorption process. By managing the production of the desired synthesis gas compositions using feed flow rates, the process conditions in the high-temperature pressure swing adsorption process can be maintained at substantially constant conditions, thus simplifying process control. In this discussion, maintaining the process conditions during the high-temperature pressure swing adsorption process at substantially constant conditions is defined as having a temperature variation of less than 10° C. and a pressure variation of less than 100 kPa at the beginning of the $CO_2$ adsorption process when processing gasification (or other pyrolysis) effluents that differ in $H_2$ content by 10 vol % or more and/or that differ in $CO_2$ content by 10 vol % or more. For example, when the gas phase pyrolysis effluent has a relatively low ratio of $H_2$ to CO, an increased portion of the gas phase effluent can be exposed to the pressure swing adsorption process. For a gas phase effluent with a higher ratio of $H_2$ to CO, an increased portion of the gas phase effluent can bypass the pressure swing adsorption process. Alternatively, if it is desired to operate the pressure swing adsorption process at a constant input flow rate, the amount of gas phase effluent that bypasses the process can be varied, depending on the feed composition. As still another option, the system can be configured to generate a fixed volume for each of one or more products. As the composition of the feed changes, the amount of synthesis gas that is exposed to adsorption conditions can be varied to generate the desired volume for each product.

In some aspects, still another advantage of the integrated gasification and swing adsorption apparatus is that multiple synthesis gas streams with different ratios of $H_2$ to CO can be generated by a single apparatus. For example, the gas phase gasification (or other pyrolysis/thermal conversion) effluent can correspond to a stream with a first ratio of $H_2$ to CO. Two or more portions of the gas phase effluent can be used as base synthesis gas streams. A remaining portion of the gas phase effluent can be passed through the high temperature swing adsorption separation stage to form an additional hydrogen stream and/or an additional synthesis gas stream with a higher ratio of $H_2$ to CO than the base synthesis gas streams. The additional hydrogen stream or additional synthesis gas stream can then be added to the base synthesis gas streams to generate streams with desired ratios of $H_2$ to CO. It is noted that the both the relative amount of biomass to plastic waste and the composition of the biomass/plastic waste can strongly influence the synthesis gas ratio in the gas phase effluent from a pyrolysis or gasification process. Thus, the systems and methods described herein provide a high degree of flexibility in producing desirable synthesis gas streams.

In some aspects, yet another advantage can be increased capture of $CO_2$. By separating $CO_2$ from the pyrolysis product using a high temperature pressure swing adsorption apparatus, an unexpected synergy can be achieved. In addition to not requiring a separate water gas shift reaction stage, additional $CO_2$ can be adsorbed. This is due to removing $CO_2$ while still in the presence of water gas shift conditions. The adsorption of $CO_2$ drives further equilibrium creation of $H_2$ and $CO_2$ (and reduction of CO and $H_2O$). By creating more $CO_2$ in-situ during the adsorption, an increased amount of $CO_2$ can be adsorbed relative to the amount initially present in the stream delivered to the adsorption step. In some aspects, 90 vol % or more of the CO in the input stream to the adsorption step can be converted to $CO_2$, or 95 vol % or more, or 98 vol % or more, such as up to substantially all of the CO. In some aspects, 80 vol % or more of the combined CO and $CO_2$ in the input stream to the adsorption step can be adsorbed as $CO_2$, or 85 vol % or more, or 90 vol % or more When forming the multiple product streams from the gasification effluent, different criteria can potentially be used as the target criteria for the composition of each stream. For example, one option for characterizing a synthesis gas stream is based on the $H_2$ to CO ratio of the stream. For Fischer-Tropsch synthesis, the $H_2$ to CO ratio, sometimes referred to as the "S-ratio", can be used to characterize the suitability of a synthesis gas stream as a feed for a Fischer-Tropsch process. Desirable S-ratio values for Fischer-Tropsch synthesis can range from 1.8 to 2.1. It is noted that the amount of $CO_2$ and $H_2O$ in a feed for Fischer-Tropsch synthesis is not critical, so long as a sufficient volume percentage of $CO_2$ and $H_2O$ are present in the stream.

Another option for characterizing a synthesis gas stream is based on the M ratio. The M-ratio is defined in Equation (1).

$$M = \frac{H_2 - CO_2}{CO + CO_2} \tag{1}$$

Characterizing a synthesis gas feed based on the M ratio can be beneficial for processes such as methanol synthesis, where some water gas shift may occur under the processing conditions and/or where $CO_2$ may otherwise serve as a reactant. Suitable M-ratios for methanol synthesis can range from 2.0 to 2.2.

Biomass and Polyolefin Feedstock

Pyrolysis (such as gasification) of biomass is a desirable pathway for formation of carbon-based fuels and products, due in part to the potential for a sustainable cycle of carbon use. This is due in part to the nature of biomass, which can be grown and harvested on a relatively short time scale. When the biomass is converted to fuel products, the resulting $CO_2$ can be consumed to form new biomass. Plastic products can partially disrupt this cycle, due to the relatively long life of many plastics. Co-processing of plastic waste with biomass via pyrolysis can provide an opportunity to add the plastic waste back to the cycle of carbon use.

The biomass used for pyrolysis can be any convenient type of biomass. Some forms of biomass can include direct forms of biomass, such as algae biomass and plant biomass. Other forms of biomass may correspond to waste products, such as food waste, animal waste, paper, and/or other waste products originally formed from biomass materials.

Some common types of plastic waste are based on plastic formed from polyolefin polymers. Polyolefin polymers are used in a wide variety of industrial and consumer applications. In some instances, substantial quantities of polymer/plastic waste may be available that correspond to a single type of polyolefin, but more typically polyolefin waste corresponds to a mixture of polyethylene, polypropylene, and/or other polymer chains based on small olefins. More generally, various types of polymers may be present in plastic waste. This can include polymers having aliphatic and/or aromatic side chains (such as polystyrene); polymers including halogen atoms (such as polyvinylchloride, polyvinylidene chloride, and partially or full fluorinated polymers); and polymers including other types of heteroatoms (such as polyesters or polyamides). In addition to polymers, plastic waste can also include any additives, modifiers, packaging dyes, and/or other components typically added to a polymer during and/or after formulation. The feedstock can further include any components typically found in polymer waste. In various aspects, the polymer content of the plastic waste feed can correspond to 51 wt % or more of the plastic waste feed, or 70 wt % or more, or 85 wt % or more, such as up to having a plastic waste feed that is substantially composed of polymer (i.e., up to 100 wt % polymer content, or having less than 1.0 wt % of non-polymer content). Finally, the feedstock can further include one or more solvents or carriers so that the feedstock to the pyrolysis process corresponds to a solution or slurry of the plastic waste.

In the feedstock, any convenient ratio of biomass to plastic waste can be used, so long as the weight of biomass is greater than the weight of plastic waste. In various aspects, relative to the combined weight of biomass and plastic waste, the biomass can correspond to 51 wt % to 99 wt % of the combined weight, or 71 wt % to 99 wt %, or 51 wt % to 90 wt %, or 71 wt % to 90 wt %. Therefore, the weight of plastic waste can correspond to 1 wt % to 49 wt % of the combined weight of biomass and plastic waste, or 1 wt % to 29 wt %, or 10 wt % to 49 wt %, or 10 wt % to 29 wt %. In some aspects, the feedstock can further include one or more solvents, carriers, diluents, and/or other materials distinct from the biomass and plastic waste. These distinct materials can correspond to 40 wt % or less of the feedstock, or 25 wt % or less, or 15 wt % or less, or 10 wt % or less, such as down to having substantially no materials other than biomass and plastic waste in the feedstock.

In various aspects, the plastic waste and/or the biomass can be prepared for incorporation into the plastic feedstock. Methods for preparing the plastic waste can include reducing the particle size of the plastic waste and mixing the plastic waste with a solvent or carrier.

In aspects where the plastic waste and/or biomass are introduced into the gasification (or other thermal conversion) reactor at least partially as solids, having a small particle size can facilitate transport of the solids into the pyrolysis reactor. Smaller particle size can potentially also contribute to achieving a desired level of conversion of the plastic waste and/or biomass under the short residence time conditions of the pyrolysis. To prepare solids for pyrolysis, the solids can be crushed, chopped, ground, or otherwise physically processed to reduce the median particle size to 3.0 cm or less, or 2.5 cm or less, or 2.0 cm or less, or 1.0 cm or less, such as down to 0.01 cm or possibly still smaller. For determining a median particle size, the particle size is defined as the diameter of the smallest bounding sphere that contains the particle.

Additionally or alternately, a solvent or carrier can be added to the feedstock. For introduction into a pyrolysis reactor, it can be convenient for the plastic waste to be in the form of a solution, slurry, or other fluid-type phase. If one or more solvents are used to at least partially solvate the polyolefins, any convenient solvent can be used. Examples of suitable solvents can include (but are not limited to) a wide range of petroleum or petrochemical products. For example, some suitable solvents include crude oil, naphtha, kerosene, diesel, and gasoils. Other potential solvents can correspond to naphthenic and/or aromatic solvents, such as toluene, benzene, methylnaphthalene, cyclohexane, methylcyclohexane, and mineral oil. Still other solvents can correspond to refinery fractions, such as a gas oil fraction or naphtha fraction from a steam cracker product. Optionally, one or more solvents can also be used to solvate at least a portion of the biomass.

Processing Conditions—Gasification

In various aspects, the plastic waste is first prepared by cutting the plastic waste into small particles and/or by dissolving the plastic waste in a solvent. Optionally, similar preparations can be performed on the biomass portion of the feedstock. The prepared feedstock can then be fed into a suitable reactor, such as a fluidized bed thermal cracker. The feedstock is then heated to a temperature between 500° C.-1200° C. for a reaction time to perform gasification, pyrolysis, or other thermal conversion. The reaction time at a temperature of 500° C. or more can be 1.0 seconds to 10 seconds. The temperature can depend in part on the desired products. Higher temperatures can increase production of $H_2$, while lower temperatures can increase selectivity for hydrocarbon products. It is noted that decomposition of both biomass and plastic waste can occur at significantly lower temperatures, such as temperatures of 400° C. or less. In some aspects, a diluent stream of steam can also be fed into the reactor as a fluidizing gas. The weight ratio of steam to feedstock can be between 0.3:1 to 10:1.

The heating and cooling of the feedstock/pyrolysis products can be performed in any convenient manner that allows for rapid heating of the feedstock. In some aspects, at least a portion of the heating of the feedstock to the pyrolysis temperature can be performed at a heating rate of 100° C./sec or more, or 200° C./sec or more, such as up to 1000° C./sec or possibly still faster. As an example, in an aspect where the pyrolysis reactor corresponds to a fluidized bed, the heating of the feedstock can be performed by mixing the feedstock with heated fluidizing particles. Sand is an example of a suitable type of particle for the fluidized bed. During operation, sand (or another type of heat transfer particle) can be passed into a regenerator to burn off coke and heat the particles. Additional heat will have to be supplied in the regenerator to compensate for the low coke make in this process. The heated particles can then be mixed with the feedstock prior to entering the reactor. By heating the heat transfer particles to a temperature above the desired pyrolysis temperature, the heat transfer particles can provide at least a portion of the heat needed to achieve the pyrolysis temperature. For example, the heat transfer particles can be heated to a temperature that is greater than the desired pyrolysis temperature by 100° C. or more. Optionally, if the feedstock, sand, and fluidizing steam does not provide sufficient material to form a fluidized bed, additional fluidizing gas can be added, such as additional nitrogen, but this also will cause a corresponding increase in the volume of gas flow that needs to be handled during product recovery. After exiting from the pyrolysis reactor, the heat transfer particles can be separated from the vapor portions of the pyrolyzed effluent using a cyclone or another solid/vapor separator. Such a separator can also remove any other solids present after pyrolysis. It is noted that separation using a cyclone separator can result in an increase in $N_2$ in the steam cracker effluent, which can make product recovery more challenging. Optionally, in addition to a cyclone or other primary solid/vapor separator, one or more filters can be included at a location downstream from the cyclone to allow for removal of fine particles that become entrained in the vapor phase.

After removing solids, the products can be cooled using a heat exchanger (or another convenient method) to a temperature of 300° C. to 500° C. to stop the reaction and recover the heat. After solids removal, the composition of the synthesis gas portion ($H_2$, CO, $CO_2$, $H_2O$) of the resulting gas phase effluent can vary widely. For example, the molar ratio of $H_2$ to CO in the gas phase effluent can be 0.5 to 1.7, or 0.5 to 1.5, or 0.8 to 1.7, or 0.8 to 1.5. As another example, the molar ratio of $H_2$ to $CO_2$ can be 0.3 to 3.0, or 0.5 to 3.0, or 1.0 to 3.0, or 0.3 to 2.5, or 0.5 to 2.5, or 1.0 to 2.5, or 0.3 to 1.0. The ratio of $H_2$ to $H_2O$ can also vary widely, and depends on various factors, including whether steam was used as a fluidizing gas, the amount of oxygen in the feedstock, and whether other sources of water were present in the feedstock and/or processing environment.

An example of a suitable reactor for performing gasification (or other pyrolysis) of a combined feed is a reverse flow reactor. Reverse flow reactors are described, for example, in U.S. Pat. No. 7,976,797 and U.S. Patent Application Publication 2019/0153331, which are incorporated herein by reference for the limited purpose of describing a suitable environment for performing a pyrolysis reaction. A reverse flow regenerative reactor is a reactor or reactor system, whereby materials flow therein for a period of time in one direction through all or selected portions of the reactor and react or are otherwise processed therein. The direction of flow is then reversed and other materials are fed from the opposite direction through the reactor to displace any remaining first materials or reaction products back in the direction opposite from the original flow. The introduced other materials also flow through the reactor for pyrolysis reaction therein. Thereby, the reactor bed or reactor media components are exposed to materials flowing in each direction through the reactor. Heat may be produced or added by the reactants flowing in one direction and that heat may be used to pyrolyze or otherwise facilitate product-generating reactions in the reactor. A substantial part of the heat is then removed during flow in the other direction. The pyrolysis reactor system includes one or more hot or heated reaction zones and a lower temperature quenching zone that serves to absorb heat from the reacted product to quench the reaction process. After cooling the reaction product, the heated quench zone is cooled by reversing the direction of flow through the reactor and feeding new supply of materials through the quench zone to absorb the quench zone heat and carry that heat back to the reaction zone where the recovered heat is conserved and reused to pre-heat the reaction zone and reactant materials. After reaction of the pre-heated reactants, the reactor is "regenerated" and ready to pyrolyze the hydrocarbonaceous reactant material (including any diluents or co-feeds) flowing through the reactor system in the opposite direction.

At least a portion of the feedstock that is transferred to or fed into the reactor system is, generally, (i) pyrolyzed (e.g., cracked) in the reaction zone to form the pyrolysis product (e.g., olefins, aromatics, and/or acetylene), and (ii) that cracked reaction product from (i) is quenched in the quenching zone to stop the reaction at the desired pyrolysis product step to thereby yield the pyrolysis product. If the reaction is not timely quenched and stopped, the reaction may continue decomposing the molecules into coke, elemental components, or other less desirable reaction product components.

Separated but simultaneous introduction of two or more reactants into the reactor system, such as through separate flow channels, can facilitate deferred reaction or combustion of the reactants until they are combined with each other, within the desired reactor zone to react with each other within that designated zone. Thereby, a heat bubble may be controllably and repeatedly positioned within the reactor system. In some embodiments, the reverse flow regenerative reactor may be described as comprising two zones/reactors: (1) a heat recuperating (first) zone/reactor, such as for quenching; and (2) a reforming (second) zone/reactor, such as for pyrolysis reaction and reforming. In some embodiments, however, the first and second reactors need not necessarily be separate components, but instead may be merely different sections of a common reactor. A reactant mixer may be provided intermediate the first and second reactors to assist with mixing and reacting of the separately introduced reactants.

The requisite high temperature required for many pyrolysis reactions may be achieved by creating a high-temperature heat bubble in the middle of the reactor system or within one of the reactors of the reactor system, such as in packed or monolithic bed system. This heat bubble may be created via a two-step process wherein heat is (1) added to the reactor bed via delayed or deferred, in-situ combustion, and then (2) removed from the bed via in-situ endothermic reforming.

Conceptually, a regenerative reverse-flow thermal pyrolysis reactor can encompass a reaction region which is abutted by first and second heat transfer zones. The reaction region can encompass a pyrolysis zone and a combustion zone. This description is conceptual in that, e.g., the pyrolysis zone and combustion zone can occupy substantially the same (or overlapping) physical space within the reactor, albeit at different times. Methods used to establish initial conditions in these zones at the start of operation are not critical. For example, if the reactor is to begin in pyrolysis mode, conventional methods can be used to preheat the reactor's first heat transfer zone and precool the second heat transfer zone, but the invention is not limited thereto. During pyrolysis mode, heat is transferred from the reactor to feed in first heat transfer zone. Sufficient heat is transferred in the first heat transfer zone to pyrolyze the heated feed in pyrolysis zone. Effluent from the pyrolysis zone (pyrolysis product) is cooled by a transfer of heat to the reactor in second heat transfer zone, which rapidly quenches the pyrolysis product. Condensable constituents that may be present in the pyrolysis product typically deposit in the second heat transfer zone. The process gas, which typically comprises the remainder of the pyrolysis product, is conducted away via line as shown. The pyrolysis is carried out for a time under pyrolysis conditions which establish a desired (typically predetermined) approach temperature at the start of at reactor location Y. Since the pyrolysis is on average endothermic, pyrolysis mode is periodically switched to heating mode, which reheats the reactor for continued pyrolysis and to establish a desired (typically predetermined) approach temperature at reactor location. A useful feature of regenerative reverse-flow thermal pyrolysis reactors is that at least part of the heat removed from the pyrolysis product during the quenching (less any radiative, conductive, and convective losses) is stored in the reactor's second heat transfer zone and is available for transfer during regeneration mode operation. Another useful feature is that at least part of the heat removed from the combustion effluent during the quenching (again, less any radiative, conductive, and convective losses) is stored in the reactor's first heat transfer zone and is available for transfer during pyrolysis mode operation.

During regeneration mode, which is carried out in an average flow direction that is substantially the reverse of the pyrolysis flow direction, oxidant and fuel are introduced into the reactor via line, which typically comprises substantially separate fuel channels and oxidant channels. The fuel and oxidant are conveyed through the second heat transfer zone toward the combustion zone. Sufficient heat is transferred from the reactor in second heat transfer zone to the fuel and air for these to combust in combustion zone. Heat is transferred from the combustion effluent to reactor first heat transfer zone. Thus, the first and second heat transfer zones are regenerated for a following forward-flow thermal pyrolysis interval, and the desired approach temperature is established at reactor location for carrying out pyrolysis mode.

Separation of $CO_2$ by Pressure Swing Adsorption

Pressure swing adsorption (PSA) relies on swinging or cycling pressure over a bed of adsorbent through a range of values. In PSA processes, a gaseous mixture is conducted under pressure for a period of time over a first bed of a solid sorbent that is selective, or relatively selective, for one or more components, usually regarded as a contaminant, to be removed from the gaseous mixture. For example, a feed can be introduced into a PSA apparatus at a feed pressure. At the feed pressure, one or more of the components (gases) in the feed can be selectively (or relatively selectively) (ad)sorbed, while one or more other components (gases) can pass through with lower or minimal adsorption. A component (gas) that is selectively (ad)sorbed can be referred to as a "heavy" component of a feed, while a gas that is not selectively (ad)sorbed can be referred to as a "light" component of a feed. For convenience, a reference to the "heavy" component of the feed can refer to all components (gases) that are selectively (ad)sorbed, unless otherwise specified. Similarly, a reference to the "light" component can refer to all components (gases) that are not selectively (ad)sorbed, unless otherwise specified. After a period of time, the feed flow into the PSA apparatus can be stopped. The feed flow can be stopped based on a predetermined schedule, based on detection of breakthrough of one or more heavy components, based on (ad)sorption of the heavy component(s) corresponding to at least a threshold percentage of the total capacity of the (ad)sorbent, or based on any other convenient criteria. The pressure in the reactor can then be reduced to a desorption pressure that can allow the selectively (ad)sorbed component(s) (gas(es)) to be released from the (ad)sorbent. Optionally, one or more purge gases, e.g. steam, can be used prior to, during, and/or after the reduction in pressure to facilitate release of the selectively (ad)sorbed component(s) (gas(es)). Depending on its nature, a full PSA cycle can optionally be performed at a roughly constant temperature. As PSA is usually enabled by at least adsorption and usually occurs on gaseous components, the terms "adsorption"/"adsorbent" and "gas(es)" are used as descriptors in the instant specification and claims, without intending to be limiting in scope, even though "absorption"/"absorbent"/"sorbent"/"sorption" and "component(s)" may be more generally applicable.

In various aspects, a synthesis gas derived from gasification (or other thermal conversion) of mixed feed of biomass and plastic waste can be used as the input flow for a high temperature pressure swing adsorption process. The synthesis gas can include $H_2$, $H_2O$, CO, and $CO_2$. In such aspects, $H_2O$ and $CO_2$ can correspond to heavy components while $H_2$ and CO can correspond to light components. During an adsorption step, $CO_2$ in the input flow can be adsorbed. As explained in more detail below, $H_2O$ is also adsorbed during the adsorption step. However, $H_2O$ (in the form of steam) is also used to regenerate the adsorbent bed in some aspects, so adsorption of $H_2O$ may simply displace other already adsorbed $H_2O$. In such aspects, adsorption of $CO_2$ will also result in desorption of $H_2O$. As a result, even though $H_2O$ is a heavy component, in some aspects net desorption of $H_2O$ may occur during the adsorption step.

The amount of $CO_2$ removed from the input flow can be greater than the initial amount present in the input flow. The water gas shift reaction is a fast equilibrium reaction under the adsorption conditions in the presence of the adsorbent. As $CO_2$ is adsorbed from the input flow, the removal of $CO_2$ drives the reaction toward producing more $CO_2$, resulting in a corresponding decrease in CO and $H_2O$ and an accompanying increase in $H_2$. Thus, even though an explicit step for removal of CO is not performed, by performing high temperature pressure swing adsorption using an adsorbent that can catalyze the water gas shift reaction, a substantial increase in the $H_2$ to CO ratio can be achieved in the product stream from the adsorption process. In some aspects, sufficient $CO_2$ adsorption can be performed so that 90 vol % or more of the CO is converted to $CO_2$. This converted $CO_2$ can then also be preferentially adsorbed.

A full pressure swing adsorption cycle involves, at a minimum, an adsorption stage (for adsorbing one or more components from an input flow) and a desorption stage (to regenerated the adsorbent by removing the adsorbed components). In order to provide a continuous or semi-continuous output flow, a plurality of adsorbent beds can be used. The multiple beds can be used to enable a complete cycle, where typically every bed sequentially goes through the same cycle. When a first PSA reactor satisfies a condition, such as the adsorbent in the reactor becoming sufficiently saturated, the feed flow can be switched to a second reactor. The first PSA reactor can then be regenerated by having the adsorbed gases released. To allow for a continuous feed flow, a sufficient number of PSA reactors and/or adsorbent beds can be used so that the first PSA reactor is finished regenerating prior to at least one other PSA reactor satisfying the condition for switching reactors.

In various aspects, a PSA reactor can be used for performing a separation on a stream containing the components of synthesis gas ($H_2O$, CO, $CO_2$ and $H_2$). In some aspects, the feed into the PSA reactor can be substantially composed of $CO_2$, CO, and $H_2$, where components of the input gas feed different from $H_2O$, $CO_2$, CO, and $H_2$ are present in an amount of about 1.0 vol % or less each, such as less than about 0.5 vol % each. Still further additionally or alternately, in a feed substantially composed of $H_2O$, $CO_2$, CO, and $H_2$, the combined vol % of components other than $H_2O$, $CO_2$, CO, and $H_2$ can be about 2.0 vol % or less, such as about 1.0 vol % or less or 0.5 vol % or less.

To perform a separation, a portion of the syngas can be introduced into a PSA reactor. Depending on the amount of cooling performed after the gasification, the syngas can have a temperature from 300° C. to 600° C., or 300° C. to 500° C., or 400° C. to 600° C. The pressure of the syngas can be 10 bar-a (~1.0 MPa-a) to 60 bar-a (~6.0 MPa-a), or 15 bar-a (~1.5 MPa-a) to 50 bar-a (~5.0 MPa-a), or 20 bar-a (~2.0 MPa-a) to 60 bar-a (~5.0 MPa-a), or 10 bar-a (~1.0 MPa-a) to 40 bar-a (~4.0 MPa-a), or 10 bar-a (~1.0 MPa-a) to 30 bar-a (~3.0 MPa-a), or 10 bar-a (~1.0 MPa-a) to 23 bar-a (~2.3 MPa-a).

When the syngas is introduced into the PSA reactor, the $H_2$ and CO in the exhaust stream corresponds to "light" components while the $H_2O$ and $CO_2$ correspond to "heavy" components. The $H_2$ can primarily pass through the reactor while the $H_2O$ and $CO_2$ can be selectively adsorbed within the reactor. Additionally, due to the water gas shift reaction, CO can be readily converted to $CO_2$. Thus, even though CO is a "light" component, the CO can be rapidly converted to "heavy" component $CO_2$ for adsorption.

The adsorption of $CO_2$ from the feed can result in a product stream that includes $H_2$, $H_2O$, and a reduced or minimized amount of CO and/or $CO_2$. In addition to enriching the product stream by removal of carbon oxides, the amount of $H_2$ in the product stream is also increased by additional $H_2$ formed by the water gas shift reaction. The amount of $H_2O$ may increase or decrease based on various factors, such as the initial feed composition, the amount of water gas shift, the amount of water desorbed from the adsorbent. The water gas shift reaction will likely consume some $H_2O$ to form $H_2$. However, in aspects where the purge stream for the adsorbent is $H_2O$, some $H_2O$ will be desorbed as $CO_2$ is adsorbed.

The feed can be passed through the high temperature PSA reactor until one or more pre-defined criteria is satisfied for switching the feed to another PSA reactor or otherwise stopping the flow of feed gas. Any convenient pre-defined criteria can be used. For example, the feed can be passed through the reactor for a specified time period. Additionally or alternately, the feed can be passed into the reactor until a breakthrough amount of $CO_2$ is detected in the product $H_2$ stream. Further additionally or alternately, the feed can be passed into the reactor until the amount of $CO_2$ that has entered the reactor is approximately equal to a threshold value of the adsorbent capacity of the reactor. In such a situation, for example, the feed can be passed into the reactor until the amount of $CO_2$ that has entered the reactor is equal to at least about 75% of the adsorbent capacity of the adsorbent material in the reactor, such as at least about 80%, at least about 85%, or at least about 90%. A typical PSA cycle can involve introducing feed into the reactor for about 30 seconds to about 300 seconds, e.g., for about 60 seconds to about 120 seconds.

After the feed is stopped, the pressure in the PSA reactor can be reduced, e.g., using one or more blow down processes or equalizations. In a blow down process, one or both sides of a PSA reactor can be opened to allow pressure to release in the form of a blow down gas stream. The blow down gas stream can generally include a majority portion of $H_2$ and can also typically include some $CO_2$. The amount of adsorbed $CO_2$ released in the blow down process(es) can depend on the nature of the adsorbent. In some conventional PSA reactors, the blow down gas stream can be exhausted from the feed input side of the reactor. Alternatively, one or more blow down gas streams can be exhausted from the product side of the reactor. For example, one option can include having an initial blow down process exiting from the product side of the reactor followed by a second blow down process allowing a gas stream to exit from both sides of the reactor. The blow down process(es) can reduce the pressure in the reactor to a value from 0.9 bar-a (~0.09 MPa-a) to 5.0 bar-a (~0.5 MPa-a), or 0.9 bar-a (~0.9 MPa-a) to 3.0 bar-a (~0.3 MPa-a), or 1.1 bar-a (~0.11 MPa-a) to 5.0 bar-a (~0.5 MPa-a), or 1.1 bar-a (~0.11 MPa-a) to 3.0 bar-a (~0.3 MPa-a). In some embodiments, maintaining a pressure above atmospheric pressure in the reactor can assist with the adsorbent retaining $CO_2$ until a subsequent purge step when desorption is desired. In some embodiments, the length of time for the blow down processes can be from about 30 seconds to about 150 seconds. At such high temperatures, a steam purge may actually be initiated with liquid water, which would vaporize upon contact with the adsorbent. This would result in increased efficiency because energy from another source would not be required to make the steam.

In some aspects, the use of multiple blow down steps can be desirable for creating blow down streams that are easier to subsequently process. For example, during adsorption of $CO_2$ from a syngas, a profile can typically develop in the reactor, with a higher content of non-adsorbed $CO_2$ near the back (input) end of the reactor and a lower content of $CO_2$ near the exit (front) end of the reactor. Based on this profile, a partial blow down from only the exit (front) end of the reactor can be used to produce a blow down output with a low $CO_2$ content. This initial blow down step can result in the higher $CO_2$ content near the back (input) end of the reactor being distributed more evenly throughout the reactor. As this occurs, it can then be more efficient to allow blow down output streams to exit from both ends of the reactor until the desired lower pressure can be achieved. Blow downs can be performed co-currently or counter-currently.

Equalization serves a dual purpose in that it transfers void space gases between adsorbent beds to raise pressure in the receiving bed while lowering pressure in transmitting bed.

Preferably, a buffer gas is not introduced into the reactor during the time between stopping the flow of exhaust gas and starting the blow down process step(s). It can additionally or alternatively be preferred that the blow down process step(s) can be performed without introducing an additional gas into the reactor. Avoiding the use of buffer gases and/or additional gases in the blow down steps can be desirable, because introduction of such gases after the flow of syngas is stopped can typically result in further loss of value into a low value stream. The blow down output flow can preferably be relatively low in $CO_2$, as it can generally be desirable to retain as much $CO_2$ as possible until the start of the subsequent purge step(s). Any $CO_2$ that exits the PSA reactor as part of a blow downstream represents additional $CO_2$ in a stream other than the desired $CO_2$ product stream. This additional $CO_2$, which can typically be in low concentration, can then need to be separately handled if it is desired to achieve as high an amount of carbon capture and recovery as possible. Thus, adding additional $CO_2$ here is also not typically desirable.

After the blow down process(es), one or more purge gas flows can be used to remove the adsorbed $CO_2$ from the reactor. One option can include using a steam purge to assist with desorbing the $CO_2$. The steam purge can be performed at a pressure from 1.0 bar-a (~100 kPa-a) to 5.0 bar-a (~500 kPa-a), or 1.0 bar-a (~100 kPa-a) to 3.0 bar-a (~300 kPa-a), or 1.1 bar-a (~110 kPa-a) to 5.0 bar-a (~500 kPa-a), or 1.1 bar-a (~110 kPa-a) to 3.0 bar-a (~300 kPa-a). An alternative option can include using a steam purge at a pressure above 3.0 bar-a (0.3 MPaa), such as a steam purge at a pressure 3.0 bar-a (~0.3 MPa-a) to 20 bar-a (~2.0 MPa-a), or 5.0 bar-a (~0.5 MPa-a) to 20 bar-a (~2.0 MPa-a), or 3.0 bar-a (~0.3 MPa-a) to 10 bar-a (~1.0 MPa-a), or 5.0 bar-a (~0.5 MPa-a) to 10 bar-a (~1.0 MPa-a). Thus, the total range for potential steam purge pressure is 1.0 bar-a (~0.1 MPa-a) to 20 bar-a (~2.0 MPa-a), or 1.1 bar-a (~0.11 MPa-a) to 20 bar-a (~2.0 MPa-a). The steam purge can result in a product $CO_2$ output stream that can also include $H_2O$ and a lesser amount of $H_2$. In some embodiments, the steam purge can last for about 25 seconds to about 150 seconds. After removal of water, the product $CO_2$ stream can have a purity of at least about 60%, e.g., at least about 65%, at least about 70%, at least about 75%, at least about 80%, at least about 85 vol %, at least about 90 vol %, at least about 92 vol %, at least about 94 vol %, at least about 95 vol %, at least about 96%, at least about 97%, at least about 98%, at least about 99%, at least about 99.3%, or at least about 99.5%. Additionally or alternately, the amount of $CO_2$ recovered can correspond to at least about 80 vol %, e.g., at least about 85 vol %, at least about 90 vol %, at least about 92 vol %, at least about 94 vol %, at least about 95 vol %, at least about 96%, at least about 97%, at least about 98%, at least about 99%, at least about 99.3%, or at least about 99.5%.

The amount of steam used in the steam purge can correspond to about 1.0 moles of water or less per mole of $CO_2$ recovered, e.g., about 0.9 moles of water or less per mole of $CO_2$ recovered, about 0.75 moles of water or less per mole of $CO_2$ recovered, about 0.6 moles of water or less per mole of $CO_2$ recovered, about 0.5 moles of water or less per mole of $CO_2$ recovered, or about 0.4 moles of water or less per mole of $CO_2$ recovered. Using less steam in the purge can be beneficial, because the amount of steam used can typically correspond to the amount of energy used for the $CO_2$ recovery. It is noted that the feed can typically contain a percentage of $H_2$. Thus, a comparison of the number of moles of water per total moles of gas (including both $H_2$ and $CO_2$) in the feed could produce still lower values, e.g., about 0.5 moles of water or less per mole of gas in the feed, about 0.4 moles of water or less per mole of gas in the feed, about 0.3 moles of water or less per mole of gas in the feed, about 0.25 moles of water or less per mole of gas in the feed, about 0.2 moles of water or less per mole of gas in the feed, about 0.15 moles of water or less per mole of gas in the feed, or about 0.1 moles of water or less per mole of gas in the feed. In such embodiments where there is a non-zero amount of steam used in the steam purge, the molar ratio of steam can be at least about 0.05 moles of water or less per mole of $CO_2$ in the feed (e.g., at least about 0.1 moles of water or less per mole of $CO_2$ in the feed, at least about 0.2 moles of water or less per mole of $CO_2$ in the feed, or at least about 0.3 moles of water or less per mole of $CO_2$ in the feed) and/or can be at least about 0.01 moles of water or less per mole of gas in the feed (e.g., at least about 0.02 moles of water or less per mole of gas in the feed, at least about 0.05 moles of water or less per mole of gas in the feed, or at least about 0.1 moles of water or less per mole of gas in the feed).

One example of a suitable adsorbent includes a mixed metal oxide adsorbent, such as an adsorbent including a mixture of an alkali metal carbonate and an alkaline earth metal oxide and/or a transition metal oxide. Examples of suitable alkali metal carbonates can include, but are not limited to, a carbonate of lithium, sodium, potassium, rubidium, cesium, or a combination thereof, e.g., a carbonate of lithium, sodium, potassium, or a combination thereof. Examples of suitable alkaline earth metal oxides can include, but are not limited to, oxides of magnesium, calcium, strontium, barium, or a combination thereof, e.g., oxides of magnesium and/or calcium. Some examples of suitable transition metal oxides can include, but are not limited to, oxides of lanthanide series metals, such as lanthanum, and/or of transition metals that can form oxides with the metal in a +2 or +3 oxidation state (such as yttrium, iron, zinc, nickel, vanadium, zirconium, cobalt, or a combination thereof).

In some aspects, the carbonate can be selected independently from the oxide in the mixed metal oxide. In such aspects, the carbonate can include, consist essentially of, or be lithium carbonate, sodium carbonate, potassium carbonate, rubidium carbonate, and/or cesium carbonate (e.g., lithium carbonate, sodium carbonate, and/or potassium carbonate; lithium carbonate and/or potassium carbonate; lithium carbonate and/or sodium carbonate; or sodium carbonate and/or potassium carbonate).

In aspects where the carbonate is selected independently from the oxide, the oxide can be an alkaline earth oxide, a transition metal oxide, a combination of two or more alkaline earth oxides, a combination of two or more transition metal oxides, or a combination of oxides including at least one alkaline earth oxide and at least one transition metal oxide. In aspects where the independently selected oxide includes one or more alkaline earth oxides, a suitable alkaline earth oxide can include, consist essentially of, or be magnesium oxide, calcium oxide, strontium oxide, and/or barium oxide, e.g., including at least magnesium oxide and/or calcium oxide. Additionally or alternatively, it may be advantageous to incorporate graphene complexes into the metal oxides to assist in adsorption.

In aspects where the independently selected oxide includes one or more transition metal oxides, suitable transition metals can include, consist essentially of, or be one or more transition metals that can form oxides with the metal in a +2 or +3 oxidation state (e.g., yttrium oxide, iron oxide, zinc oxide, nickel oxide, vanadium oxide, cobalt oxide, zirconium oxide, lanthanum oxide, other oxides of lanthanide metals, and/or a combination thereof). One preferred option includes a transition metal oxide selected from lanthanum oxide and/or zirconium oxide. Another option includes a metal oxide selected from lanthanum oxide, yttrium oxide, zirconium oxide, and/or zinc oxide. Yet another option includes a metal oxide selected from nickel oxide, cobalt oxide, and/or iron oxide. Mixtures within each of these options and/or across options are also contemplated, such as mixtures of lanthanum oxide with zinc oxide and/or vanadium oxide; mixtures of lanthanum oxide with iron oxide, cobalt oxide, and/or nickel oxide; mixtures of zirconium oxide with yttrium oxide, zinc oxide, and/or vanadium oxide; and mixtures of zirconium oxide with iron oxide, cobalt oxide, and/or nickel oxide.

In aspects where the independently selected oxide includes one or more alkali metal oxides and one or more transition metal oxides, suitable alkali metal oxides can include, consist essentially of, or be magnesium oxide, calcium oxide, strontium oxide, and/or barium oxide, while suitable transition metals can include, consist essentially of, or be transition metals that can form oxides with the metal in a +2 or +3 oxidation state, such as yttrium oxide, iron oxide, zinc oxide, nickel oxide, vanadium oxide, cobalt oxide, zirconium oxide, lanthanum oxide, and/or other lanthanide oxides. Each of these alkali metal oxides and transition metal oxides can be independently selected individually or in any combination of multiple transition metal oxides. Examples of mixtures can include, consist essentially of, or be a mixture of oxides where at least one oxide is lanthanum oxide, zirconium oxide, and/or magnesium oxide; a mixture of oxides where the mixture includes at least two of lanthanum oxide, zirconium oxide, and magnesium oxide; a mixture of oxides where one oxide is magnesium oxide and/or calcium oxide; and/or a mixture of oxides where at least one oxide is lanthanum oxide, yttrium oxide, and/or zirconium oxide.

In some alternative aspects, a mixed metal oxide can include an alkaline earth carbonate in combination with a transition metal oxide. In such aspects, the alkaline earth carbonate can include, consist essentially of, or be magnesium carbonate and/or calcium carbonate. Additionally or alternately, the alkaline earth carbonate can be present in a mixture with an alkali metal carbonate. Examples of such carbonate mixtures can include, consist essentially of, or be mixtures of lithium carbonate with magnesium carbonate, lithium carbonate with calcium carbonate, potassium carbonate with magnesium carbonate, potassium carbonate with calcium carbonate, sodium carbonate with magnesium carbonate, and sodium carbonate with calcium carbonate (e.g., lithium carbonate with magnesium carbonate or potassium carbonate with magnesium carbonate). In such aspects, suitable transition metals can include, consist essentially of, or be transition metals that can form oxides with the metal in a +2 or +3 oxidation state, such as yttrium oxide, iron oxide, zinc oxide, nickel oxide, vanadium oxide, cobalt oxide, zirconium oxide, lanthanum oxide, other lanthanide oxides, and/or a combination thereof. Each of these alkaline earth carbonates and transition metal oxides can be independently selected individually or in any combination of multiple alkaline earth carbonates and/or multiple transition metal oxides. For the transition metal oxide, one preferred option can include a transition metal oxide selected from lanthanum oxide or zirconium oxide. Another option can include a metal oxide selected from lanthanum oxide, yttrium oxide, zirconium oxide, and/or zinc oxide. Yet another option can include a metal oxide selected from nickel oxide, cobalt oxide, and/or iron oxide. Mixtures within each of these options and/or across options are also contemplated, such as mixtures of oxides where at least one oxide is lanthanum oxide and/or zirconium oxide; mixtures of lanthanum oxide with zinc oxide and/or vanadium oxide; mixtures of lanthanum oxide with iron oxide, cobalt oxide, and/or nickel oxide; mixtures of zirconium oxide with yttrium oxide, zinc oxide, and/or vanadium oxide; and/or mixtures of zirconium oxide with iron oxide, cobalt oxide, and/or nickel oxide. Additional or alternative materials can include hydrotalcites.

In using such materials at high temperatures, it has been found that the WGS reaction and $CO_2$ adsorption can occur nearly simultaneously.

In another aspect, the adsorbent particles can be assembled into an ordered structure such as a monolith. Conventional monolith adsorbents have their own characteristic advantages and disadvantages, one of which is that it is difficult to form a thin and reliably uniform wash coating of adsorbent on the support, especially if the monolith has pores of relatively small diameter when the coating solution may clog the pore entrances and preclude further ingress of coating material. In this case, the adsorption characteristics of the monolith are likely to be unpredictable and less than optimal. To overcome this drawback, while retaining advantages of the monolith to a certain extent, including its low tortuosity and predictable void volume, particulate adsorbents can preferably be formed into a simulated monolith by laying down a layer of the adsorbent material on the surfaces of the particles and then assembling the particles into the adsorbent bed, e.g., either by packing directly into the sorption vessel in a densely packed bed or, more preferably, by forming the coated structured adsorbent particles into shaped structures which can then be packed into the vessel in the form of blocks, similarly to blocks of monolith. In effect, the conventional method of monolith fabrication can be inverted and the adsorbent coated onto the outside of the support particles and the monolith-like structure then assembled from the coated particles. In this way, not only can a more uniform coating of the essential adsorbent be achieved but the pore structure of the simulated monolith can be controlled by using particles of different shapes and surface roughness. When operating in this manner, the adsorbent particles should have a ratio of length to maximum cross-sectional dimension ratio of at least 2:1, preferably at least 5:1, and a maximum cross-sectional dimension typically not more than 5 mm, for example not more than 1 mm After the particles are laid down in the ordered configuration with longitudinally extensive, substantially aligned gas channels, the particles can then be bundled/adhered together in the mass to form a coherent, self-supporting body. The masses can then be placed in the vessel with the gas passages aligned in the desired orientation to form an ordered adsorbent bed. The void fraction within the adsorbent—that is, the ratio of the void volume due to porosity of solid adsorbents (including micropores and macropores) and also void volume due to gas flow channels or interstices to the volume of the vessel containing the adsorbent—should be less than 0.5, or less than 0.3.

CONFIGURATION EXAMPLES

The FIGURE shows a process flow for integration of a gasification process with a high temperature pressure swing adsorption process for processing mixed feeds of plastic waste and biomass to produce multiple synthesis gas streams. In the FIGURE, a biomass feed 112 and a plastic waste feed 114 are passed into a gasification (or other thermal conversion) process 120. The gasification process 120 forms at least a gas phase effluent 125 that includes synthesis gas or that is substantially composed of synthesis gas. The gas phase effluent 125 represents the effluent after any solids removal (not shown). The gas phase effluent 125 is then split into at least portions. The at least three portions include two or more bypass portions, such as first bypass portion 133 and a second bypass portion 137, and a portion that is used as input flow 131 into pressure swing adsorption process 140. Pressure swing adsorption process 140 can generate a hydrogen-enriched product 145 and a $CO_2$-enriched purge stream 148. A first portion 153 of the hydrogen-enriched product 145 can then be combined with first bypass portion 133 to form a first product 163, such as a product with a $H_2$ to CO ratio that is suitable for Fischer-Tropsch synthesis. A second portion 157 of the hydrogen-enriched product 145 can be combined with the second bypass portion 137 to form a second product 167, such as a product with a content of $H_2$, CO, and $CO_2$ that is suitable for methanol synthesis.

Example—Generation of Multiple Synthesis Gas Streams from Variable Gasification Output Streams This example shows calculations for using a high temperature swing adsorber to process a portion of a gasification effluent in order to make a plurality of improved synthesis gas streams. In the calculations, it is assumed that a) all CO is converted to $CO_2$ by water gas shift, b) adsorption of $CO_2$ is 100%, so that the $H_2$-enriched product stream contains substantially no CO or $CO_2$, and c) 95% of the $H_2$ is recovered as part of the $H_2$-enriched product stream.

In this example, a portion of a gasification effluent is processed using a high temperature pressure swing adsorber to form an $H_2$-enriched product stream. Portions of the $H_2$-enriched product stream are then added to additional portions of the gasification effluent to make a methanol synthesis feedstock and a Fischer-Tropsch synthesis feedstock. The methanol synthesis feedstock has a target M-ratio of 2.05, while the Fischer-Tropsch synthesis feedstock had an S-ratio of 1.9.

Table 1 shows two model input flows to the pressure swing adsorption process that were used for the calculations. The model feeds represent the potentially widely varying nature of the synthesis gas produced by a gasification process when using biomass and plastic waste as the feedstock. It is noted that the mol % values in the table refer only to $H_2$, CO, and $CO_2$. Various amounts of water could be present. The amount of water is not strictly relevant so long as sufficient water is available for conversion of CO to $CO_2$ by water gas shift. For the feeds shown in Table 1, an initial input flow of 100 kmol/hr was used. This initial input flow was then divided to form an input feed for the adsorption step and a remaining portion that is supplemented with the $H_2$-enriched product stream to form a desired synthesis gas.

TABLE 1

| | Input Flows to Adsorber | | | | |
|---|---|---|---|---|---|
| | $H_2$ (mol %) | CO (mol %) | $CO_2$ (mol %) | Input Feed rate to Adsorber (kmol/hr) | First Bypass Amount (kmol/hr) |
| Feed 1 | 0.2 | 0.3 | 0.5 | 97.3 | 2.7 |
| Feed 2 | 0.5 | 0.3 | 0.2 | 84.3 | 15.7 |

As shown in Table 1, Feed 1 had a molar ratio of $H_2$ to CO of 0.67, corresponding to a relatively low quality synthesis gas feed. Additionally, Feed 1 had a relatively high $CO_2$ content. Feed 2 had a higher molar ratio of $H_2$ to CO of 1.67, with a relatively low $CO_2$ content.

Table 2 shows the resulting product flows from the adsorption, and the amount of the methanol synthesis feedstock that is formed by combining a portion of the $H_2$-enriched product with the first bypass portion of the feed. Note that in the column for the amount of $H_2$-enriched product that is added to the first bypass amount, the amount of the first bypass stream is shown in parentheses.

TABLE 2

Formation of Methanol Synthesis Stream

| | $H_2$-enriched Product (kmol/hr) | Tail gas ($H_2$ + $CO_2$) (kmol/hr) | $H_2$-enriched product combined with First Bypass (kmol/hr) | $H_2/CO/CO_2$ molar ratio in combined product | M-ratio |
|---|---|---|---|---|---|
| Feed 1 | 18.5 | 78.8 | 5.3 (+2.7) | 0.73/0.10/0.17 | 2.05 |
| Feed 2 | 40.1 | 44.3 | 11.4 (+15.7) | 0.71/0.17/0.12 | 2.05 |

Table 3 shows formation of the Fischer-Tropsch synthesis gas stream. The remaining portion of the $H_2$-enriched product is combined with a sufficient amount of a second portion of bypassed gasification effluent to form a synthesis gas stream with an S-ratio of roughly 1.9. It is noted that the second bypassed amount is considerably larger than the first bypassed amount. In various aspects, the relative amounts of a first product and a second product can be varied to achieve desired volumes of targeted synthesis gas feeds.

TABLE 2

Formation of Fischer-Tropsch Synthesis Stream

| | $H_2$-enriched Product (kmol/hr) | Tail gas ($H_2$ + $CO_2$) (kmol/hr) | $H_2$-enriched product combined with Second Bypass (kmol/hr) | $H_2/CO/CO_2$ molar ratio in combined product | S-ratio |
|---|---|---|---|---|---|
| Feed 1 | 18.5 | 78.8 | 13.2 (+36) | 0.41/0.22/0.37 | 1.89 |
| Feed 2 | 40.1 | 44.3 | 28.6 (+400) | 0.53/0.28/0.19 | 1.90 |

Additional Embodiments

Embodiment 1. A method for forming a plurality of synthesis gas compositions, comprising: exposing a feedstock comprising a mixture of biomass and plastic waste to pyrolysis conditions at a temperature of 500° C. to 1200° C. to form at least a low-hydrogen-content synthesis gas stream comprising $H_2$, CO, and $CO_2$, the low-hydrogen-content synthesis gas stream comprising a molar ratio of $H_2$ to CO of 0.5 to 1.7; exposing at least a portion of the low-hydrogen-content synthesis gas stream to an adsorbent at a first adsorbing temperature of 300° C. to 600° C. and a first adsorbing pressure of 1.0 MPa-g or more to form an $H_2$-enriched stream comprising an $H_2$ to CO ratio of 10 or more; combining a first portion of the $H_2$-enriched stream with a first bypass portion of the low hydrogen content synthesis gas stream to form a first product synthesis gas stream comprising a first $H_2$ to CO ratio of 1.8 or more; and combining a second portion of the $H_2$-enriched stream with a second bypass portion of the low hydrogen content synthesis gas stream to form a second product synthesis gas stream comprising a second $H_2$ to CO ratio of 1.8 or more, the feedstock optionally further comprising at least one of a solvent and a carrier.

Embodiment 2. The method of Embodiment 1, wherein the $H_2$-enriched stream comprises 5.0 mol % or less of CO, 10 mol % or less of $CO_2$, or a combination thereof.

Embodiment 3. The method of any of the above embodiments, wherein the pyrolysis conditions comprise gasification conditions.

Embodiment 4. The method of any of the above embodiments, wherein the first product synthesis gas stream comprises an S-ratio of 1.8-2.1, or wherein the second product synthesis gas stream comprises an M-ratio of 1.9-2.2, or a combination thereof.

Embodiment 5. The method of any of the above embodiments, wherein the feedstock comprises 51 wt % or more of biomass relative to a combined weight of the biomass and the plastic waste.

Embodiment 6. The method of any of the above embodiments, wherein the at least a portion of the low-hydrogen-content synthesis gas stream comprises 10 mol % or more of $H_2O$.

Embodiment 7. The method of any of the above embodiments, further comprising desorbing $CO_2$ from the adsorbent at a pressure of 5.0 MPa-g or less, and optionally wherein desorbing $CO_2$ from the adsorbent comprises exposing the adsorbent to a purge stream of $H_2O$.

Embodiment 8. The method of any of the above embodiments, further comprising physically processing at least a portion of the plastic waste, at least a portion of the biomass, or a combination thereof prior to exposing the feedstock to the thermal conversion conditions to form particles having a median particle size of 3.0 mm or less.

Embodiment 9. The method of any of the above embodiments, wherein the adsorbent comprises a mixed metal oxide adsorbent.

Embodiment 10. The method of Embodiment 9, wherein the mixed metal oxide adsorbent comprises an alkali metal carbonate, an alkaline earth metal carbonate, or a combination thereof; or wherein the mixed metal oxide adsorbent comprises an alkaline earth oxide, a transition metal oxide, or a combination thereof.

Embodiment 11. The method of any of the above embodiments, wherein exposing at least a portion of the low-hydrogen-content synthesis gas stream to an adsorbent comprises performing a water gas shift reaction on the at least a portion of the low-hydrogen-content synthesis gas stream, wherein optionally at least a portion of the water for performing the water gas shift reaction comprises water desorbed from the adsorbent.

Embodiment 12. The method of any of the above embodiments, further comprising: exposing a second feedstock comprising a mixture of biomass and plastic waste to pyrolysis conditions at a temperature of 500° C. to 1200° C. to form at least a second low hydrogen content synthesis gas stream comprising $H_2$, CO, and $CO_2$, the second low-hydrogen-content synthesis gas stream comprising i) a second hydrogen content that differs from a hydrogen content of the low-hydrogen-content synthesis gas stream by 10 vol % or more, ii) a second $CO_2$ content that differs from a $CO_2$ content of the low hydrogen content synthesis gas stream by 10 vol % or more, or iii) a combination of i) and ii); exposing at least a portion of the second low-hydrogen-content synthesis gas stream to an adsorbent at a second adsorbing temperature of 300° C. to 600° C. and a second adsorbing pressure of 1.0 MPa-g or more to form a second $H_2$-enriched stream comprising an $H_2$ to CO ratio of 10 or more, the second adsorbing temperature differing from the first temperature by 10° C. or less and the second adsorbing pressure differing from the first pressure by 100 kPa or less; combining a first portion of the second $H_2$-enriched stream with a third bypass portion of the low hydrogen content synthesis gas stream to form a third product synthesis gas stream comprising a first $H_2$ to CO ratio of 1.8 or more; and combining a second portion of the $H_2$-enriched stream with a fourth bypass portion of the low hydrogen content synthesis gas stream to form a fourth product synthesis gas stream comprising a second $H_2$ to CO ratio of 1.8 or more.

Embodiment 13. The method of any of the above embodiments, wherein exposing a feedstock comprising a mixture of biomass and plastic waste to pyrolysis conditions comprising forming a pyrolysis effluent comprising 10 vol % or more hydrocarbons, the method further comprising separating the pyrolysis effluent to form the low-hydrogen-content synthesis gas stream, the separating the pyrolysis effluent to form the low-hydrogen-content synthesis gas stream optionally further comprising forming a low-hydrogen-content synthesis gas stream with an $H_2O$ content of 10 vol % or less.

Embodiment 14. The method of any of the above embodiments, wherein the low-hydrogen-content synthesis gas is formed and exposed to the adsorbent without exposing the low-hydrogen-content synthesis gas to a temperature of 100° C. or less.

Embodiment 15. The method of any of the above embodiments, wherein the feedstock is exposed to the pyrolysis conditions in a reactor by flowing the feedstock in a first direction within the reactor, the method further comprising regenerating the reactor by performing combustion in the reactor, the regenerating comprising flowing the combustion products within the reactor in a second direction different from the first direction.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

The invention claimed is:

1. A method for forming a plurality of synthesis gas compositions, comprising:
exposing a feedstock comprising a mixture of biomass and plastic waste to pyrolysis conditions at a temperature of 500° C. to 1200° C. to form at least a low-hydrogen-content synthesis gas stream comprising $H_2$, CO, and $CO_2$, the low-hydrogen-content synthesis gas stream comprising a molar ratio of $H_2$ to CO of 0.5 to 1.7;
exposing at least a portion of the low-hydrogen-content synthesis gas stream to an adsorbent at a first adsorbing temperature of 300° C. to 600° C. and a first adsorbing pressure of 1.0 MPa-g or more to form an $H_2$-enriched stream comprising an $H_2$ to CO ratio of 10 or more;
combining a first portion of the $H_2$-enriched stream with a first bypass portion of the low hydrogen content synthesis gas stream to form a first product synthesis gas stream comprising a first $H_2$ to CO ratio of 1.8 or more; and
combining a second portion of the $H_2$-enriched stream with a second bypass portion of the low hydrogen content synthesis gas stream to form a second product synthesis gas stream comprising a second $H_2$ to CO ratio of 1.8 or more.

2. The method of claim 1, wherein the $H_2$-enriched stream comprises 5.0 mol % or less of CO, 10 mol % or less of $CO_2$, or a combination thereof.

3. The method of claim 1, wherein the pyrolysis conditions comprise gasification conditions.

4. The method of claim 1, wherein the first product synthesis gas stream comprises an S-ratio of 1.8-2.1, or wherein the second product synthesis gas stream comprises an M-ratio of 1.9-2.2, or a combination thereof.

5. The method of claim 1, wherein the feedstock is exposed to the pyrolysis conditions in a reactor by flowing the feedstock in a first direction within the reactor, the method further comprising regenerating the reactor by performing combustion in the reactor, the regenerating comprising flowing the combustion products within the reactor in a second direction different from the first direction.

6. The method of claim 1, wherein the feedstock comprises 51 wt % or more of biomass relative to a combined weight of the biomass and the plastic waste.

7. The method of claim 1, wherein the at least a portion of the low-hydrogen-content synthesis gas stream comprises 10 mol % or more of $H_2O$.

8. The method of claim 1, further comprising desorbing $CO_2$ from the adsorbent at a pressure of 5.0 MPa-g or less.

9. The method of claim 8, wherein desorbing $CO_2$ from the adsorbent comprises exposing the adsorbent to a purge stream of $H_2O$.

10. The method of claim 1, further comprising physically processing at least a portion of the plastic waste, at least a portion of the biomass, or a combination thereof prior to exposing the feedstock to the thermal conversion conditions to form particles having a median particle size of 3.0 mm or less.

11. The method of claim 1, wherein the feedstock further comprises at least one of a solvent and a carrier.

12. The method of claim 1, wherein the adsorbent comprises a mixed metal oxide adsorbent.

13. The method of claim 12, wherein the mixed metal oxide adsorbent comprises an alkali metal carbonate, an alkaline earth metal carbonate, or a combination thereof.

14. The method of claim 12, wherein the mixed metal oxide adsorbent comprises an alkaline earth oxide, a transition metal oxide, or a combination thereof.

15. The method of claim 1, wherein exposing at least a portion of the low-hydrogen-content synthesis gas stream to an adsorbent comprises performing a water gas shift reaction on the at least a portion of the low-hydrogen-content synthesis gas stream.

16. The method of claim 15, wherein at least a portion of the water for performing the water gas shift reaction comprises water desorbed from the adsorbent.

17. The method of claim 1, further comprising:
exposing a second feedstock comprising a mixture of biomass and plastic waste to pyrolysis conditions at a temperature of 500° C. to 1200° C. to form at least a second low hydrogen content synthesis gas stream comprising $H_2$, CO, and $CO_2$, the second low-hydrogen-content synthesis gas stream comprising i) a second hydrogen content that differs from a hydrogen content of the low-hydrogen-content synthesis gas stream by 10 vol % or more, ii) a second $CO_2$ content that differs from a $CO_2$ content of the low hydrogen content synthesis gas stream by 10 vol % or more, or iii) a combination of i) and ii);

exposing at least a portion of the second low-hydrogen-content synthesis gas stream to an adsorbent at a second adsorbing temperature of 300° C. to 600° C. and a second adsorbing pressure of 1.0 MPa-g or more to form a second $H_2$-enriched stream comprising an $H_2$ to CO ratio of 10 or more, the second adsorbing temperature differing from the first temperature by 10° C. or less and the second adsorbing pressure differing from the first pressure by 100 kPa or less;

combining a first portion of the second $H_2$-enriched stream with a third bypass portion of the low hydrogen content synthesis gas stream to form a third product synthesis gas stream comprising a first $H_2$ to CO ratio of 1.8 or more; and combining a second portion of the $H_2$-enriched stream with a fourth bypass portion of the low hydrogen content synthesis gas stream to form a fourth product synthesis gas stream comprising a second $H_2$ to CO ratio of 1.8 or more.

18. The method of claim 1, wherein exposing a feedstock comprising a mixture of biomass and plastic waste to pyrolysis conditions comprising forming a pyrolysis effluent comprising 10 vol % or more hydrocarbons, the method further comprising separating the pyrolysis effluent to form the low-hydrogen-content synthesis gas stream.

19. The method of claim 18, wherein separating the pyrolysis effluent to form the low-hydrogen-content synthesis gas stream comprises forming a low-hydrogen-content synthesis gas stream with an $H_2O$ content of 10 vol % or less.

20. The method of claim 1, wherein the low-hydrogen-content synthesis gas is formed and exposed to the adsorbent without exposing the low-hydrogen-content synthesis gas to a temperature of 100° C. or less.

* * * * *